United States Patent [19]
Marik et al.

[11] Patent Number: 5,800,546
[45] Date of Patent: Sep. 1, 1998

[54] IMPACTOR APPARATUS FOR ASSEMBLING MODULAR ORTHOPEDIC PROSTHESIS COMPONENTS

[75] Inventors: Greg Marik; Scott Mladsi; Michael Cooper, all of Memphis, Tenn.

[73] Assignee: Smith & Nephew, Inc., Memphis, Tenn.

[21] Appl. No.: 514,798

[22] Filed: Aug. 14, 1995

[51] Int. Cl.$^6$ ............................................. A61F 2/28
[52] U.S. Cl. .................. 623/16; 606/99; 606/100; 606/92
[58] Field of Search .................. 623/16; 606/92, 606/93, 94, 99, 100, 105

[56] References Cited

U.S. PATENT DOCUMENTS

| | | | |
|---|---|---|---|
| 4,993,410 | 2/1991 | Kimsey | 606/100 |
| 4,995,883 | 2/1991 | Demane et al. | 623/23 |
| 5,108,452 | 4/1992 | Fallin | 623/23 |
| 5,314,479 | 5/1994 | Rockwood, Jr. et al. | 623/22 |
| 5,470,336 | 11/1995 | Ling et al. | 623/16 |

*Primary Examiner*—Paul B. Prebilic
*Attorney, Agent, or Firm*—Pravel, Hewitt, Kimball & Krieger

[57] ABSTRACT

An impactor apparatus and method for assembling modular orthopedic prosthesis parts includes a base member that can be for example an instrument from a tray or an instrument tray lid. The base member defines a plane and provides a plurality of components extending away from the plane. The tray components include a pair of spaced apart supports. An impactor tool can be removably supported upon the supports in a fixed position relative to the base member, preferably generally parallel thereto. The components include an impact driver tool actuator that pivotally attaches to the base member. A pair of prosthesis parts or components are connectable at a taper lock connection defined by respective tapered annular portions of the prosthesis parts. The components and impact driver tool support the prosthesis parts adjacent the base and axial alignment with the impact driver tool, the prosthesis parts being generally positioned in between the pair of spaced apart supports. The impact driver tool provides an actuator for activating the driver to transmit a load to the prosthesis parts for driving the parts together at the taper lock connection. The spaced apart supports of the base hold opposite end portions of the assembly of the prosthesis and impact driver in fixed relation to the base member.

10 Claims, 5 Drawing Sheets

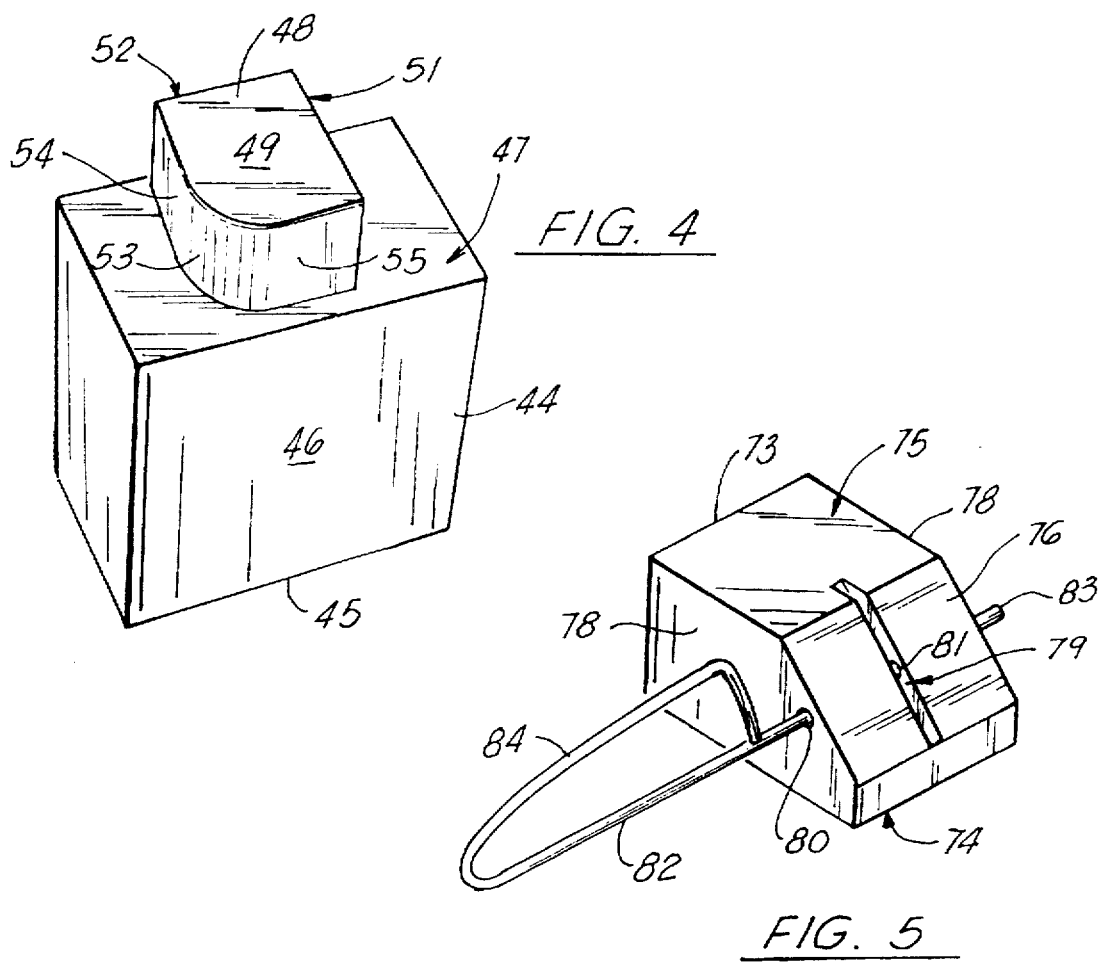
FIG. 4
FIG. 5
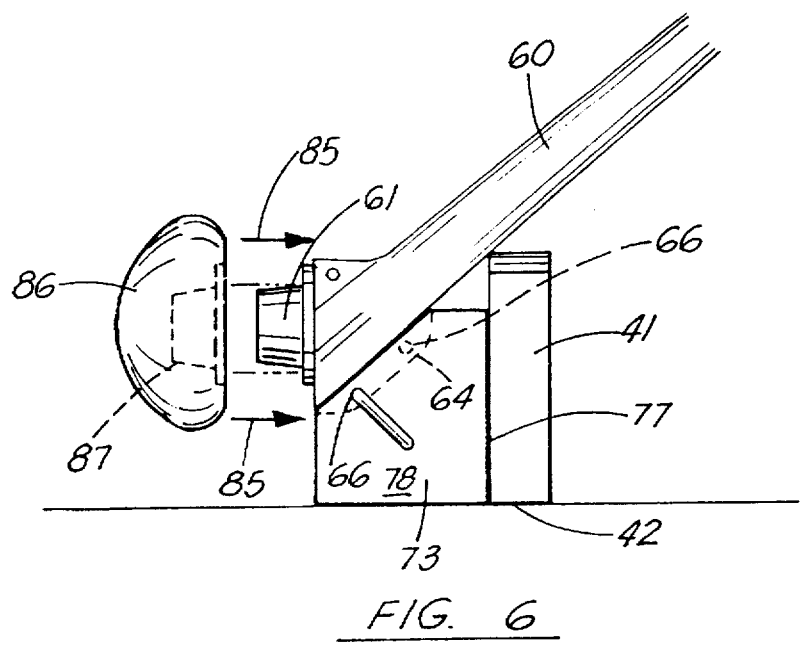
FIG. 6

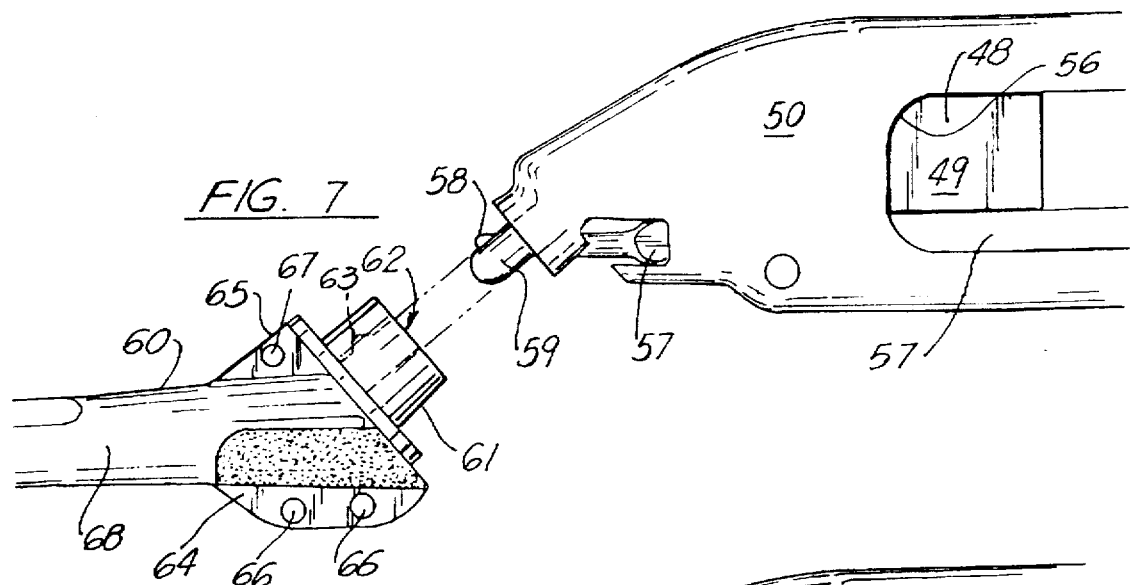
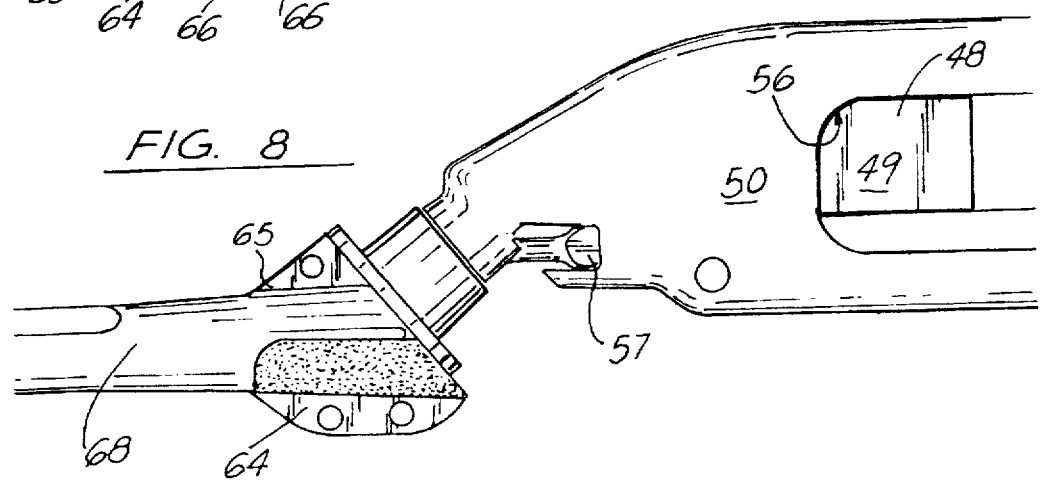
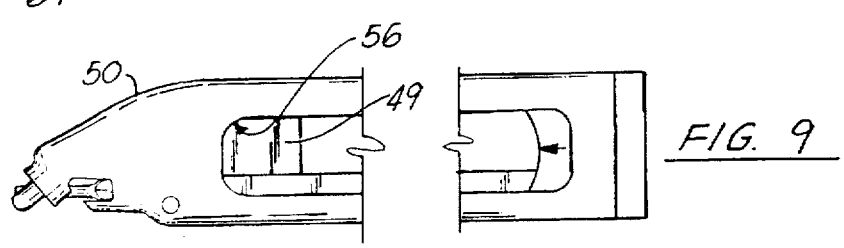
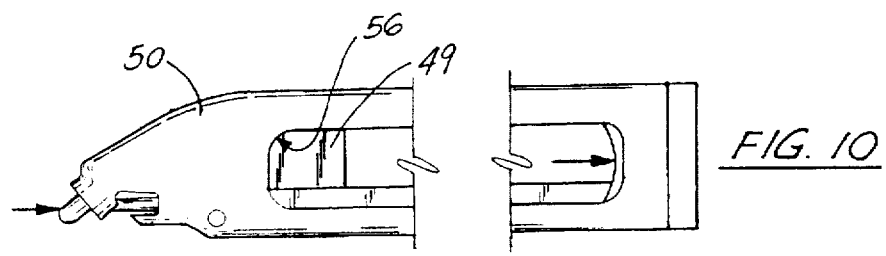

IMPACTOR APPARATUS FOR ASSEMBLING MODULAR ORTHOPEDIC PROSTHESIS COMPONENTS

BACKGROUND OF THE INVENTION

1. Field of the Invention

The present invention relates to orthopedic surgical instruments and more particularly relates to an improved method and apparatus for assembling modular orthopedic prosthesis components using an impactor tool or impact driver. Even more particularly, the present invention relates to an improved impact driver apparatus for assembling modular orthopedic prosthesis parts wherein a base member and spaced apart supports carry all of the axial load transmitted from the impact driver to the prosthesis so that the axial load is reproducible and accurate notwithstanding the rigidity of any underlying surface adjacent the base member.

2. General Background

Various orthopedic prosthetic devices are used to replace diseased tissue of the patient, for example at a joint such as the knee, hip or shoulder. Various orthopedic prosthetic devices include two or more components that can be assembled together to define the final prosthesis. These "modular" prosthetic devices are sometimes assembled using a taper lock or wedge lock connection. For example, the DeMane U.S. Pat. Nos. 4,995,883 and 5,108,452 relate to a modular hip prosthesis and its method of assembly. In the DeMane '883 and '452 patents, taper lock connections are used to assemble a distal sleeve to a hip prosthesis, and the assembly of a modular sphere or ball with a taper lock or wedge lock connection to an extension trunion.

One of the problems with modular prosthetic devices is the problem of accurate and reproducible assembly loads. In orthopedic surgery, impact driver instruments and the prosthesis to be assembled are usually supported upon an operating room table or like supporting surface. The rigidity of such an underlying support can vary from one operating room to the next. However, most impact driver tools only provide a single load setting. If the impact driver tool is supported in the hand of a user and the prosthesis braced against an operating room table, part of the load is absorbed by the underlying operating room table. This procedure can destroy predictability of the axial load actually transmitted directly to the modular prosthesis joint. When a taper lock connection is loaded in this somewhat unpredictable fashion, it is possible that a particular prosthesis could become disassembled or loose after surgical implantation.

SUMMARY OF THE INVENTION

The present invention provides a method and apparatus for transmitting axial load from an impact driver tool to a taper lock assembled modular prosthesis so that the axial load is reproducible and accurate notwithstanding the rigidity of the underlying surface such as a operating room table or the like.

The apparatus of the present invention provides a base member defining a plane and having a plurality of components that extend away from the plane on one side of the base member.

In the preferred embodiment, the base member is an instrument tray or an instrument tray lid. The impact driver, the modular prosthesis and prosthesis extension parts can be packaged in an instrument tray. The tray or lid can then function as the support for axial load transfer during impact driving.

The components extending from the base member include a pair of spaced apart supports. An impact driver tool can be removably attached to these supports. The components also include an impactor tool actuator that can be a lever pivotally attached to the base member.

A pair of prosthesis parts are connectable at a taper lock connection defined by respective tapered annular portions of the prosthesis parts. These respective tapered annular portions are placed end to end with tapered annular portions engaged.

The prosthesis parts are then held adjacent the base in axial alignment and with the impact driver engaging one of the two prosthesis parts. This assembly of prosthesis parts and impact driver is supported adjacent the tray or base, generally in-between the pair of spaced apart supports.

The actuator can then be used to activate the impact driver to thereby transmit a load to the prosthesis parts for driving the parts together at the taper lock connection. The spaced apart supports hold opposite end portions of the entire assembly of prosthesis parts and impact driver.

The base member and its components (including the supports and the actuator) carry all of the axial load transmitted from the impact driver to the prosthesis. In the fashion, the axial load is reproducible and accurate notwithstanding the rigidity of any underlying surfaces adjacent the base member. This result follows because then the base member is placed on the underlying surface whereas the load is transferred axially relative to the base member in a direction generally parallel to the underlying surface. A load is thus transmitted through the base member and its components, providing a constant load transmission system that is reproducible and accurate.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 4 is a fragmentary view of the preferred embodiment of the apparatus of the present invention illustrating one of the support components;

FIG. 5 is another fragmentary view of the preferred embodiment of the apparatus of the present invention illustrating another of the support components;

FIG. 6 is a fragmentary elevational view illustrating an assembly of two prosthesis parts together, a shoulder stem and head portion;

FIG. 7 is a fragmentary view illustrating an assembly of a shoulder stem prosthesis portion to a handle used for manipulating the shoulder stem;

FIG. 8 is a fragmentary view illustrating an assembly of a shoulder stem prosthesis portion to a handle used for manipulating the shoulder stem;

FIG. 9 is a fragmentary view of the preferred embodiment of the apparatus of the present invention illustrating the handle of FIGS. 7 and 8 in a locked position;

FIG. 10 is a fragmentary view of the preferred embodiment of the apparatus of the present invention illustrating the handle of FIGS. 7 and 8 in an unlocked position.

DETAILED DESCRIPTION OF THE PREFERRED EMBODIMENT

Figure 1:
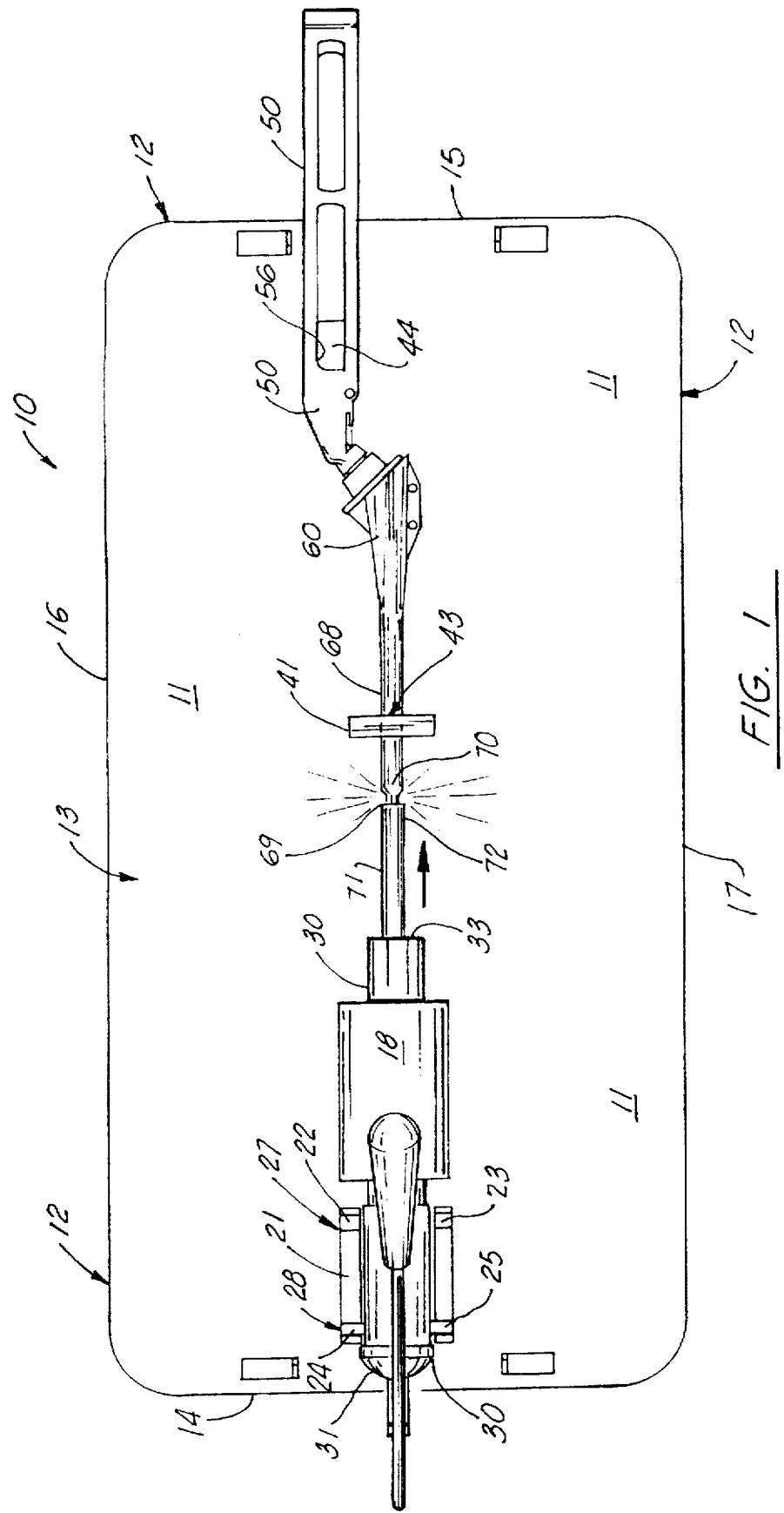
FIG. 1 is a top plan view of the preferred embodiment of the apparatus of the present invention showing the impacting of a distal extension member to a stem.

FIGS. 1-3 and 3A show generally the preferred embodiment of the apparatus of the present invention designated generally by the numeral 10. Prosthesis impactor apparatus 10 includes a base member 11 that can be for example an instrument tray or an instrument tray lid. If an instrument tray or lid is used as base member 11, such can be constructed of structurally sound material such as stainless steel for example.

The base member 11 includes a periphery 12 and an upper surface 13 that is flat, defining a plane. Base member 11 includes end portions 14, 15 and side portions 16, 17.

Figure 2:
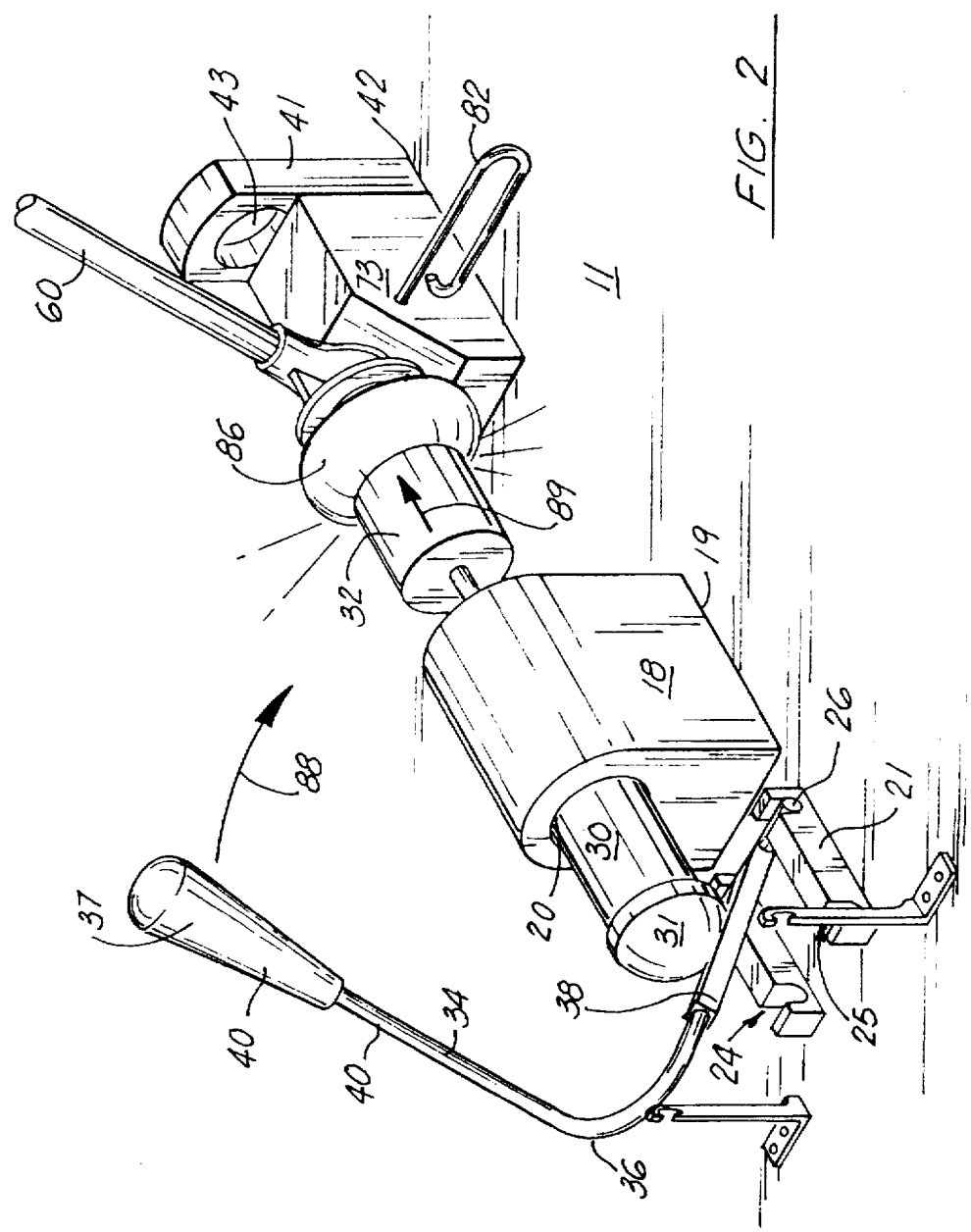
FIG. 2 is a perspective view of the preferred embodiment of the apparatus of the present invention illustating the impacting of a modular head being affixed to a prosthesis stem.
Figure 3A:
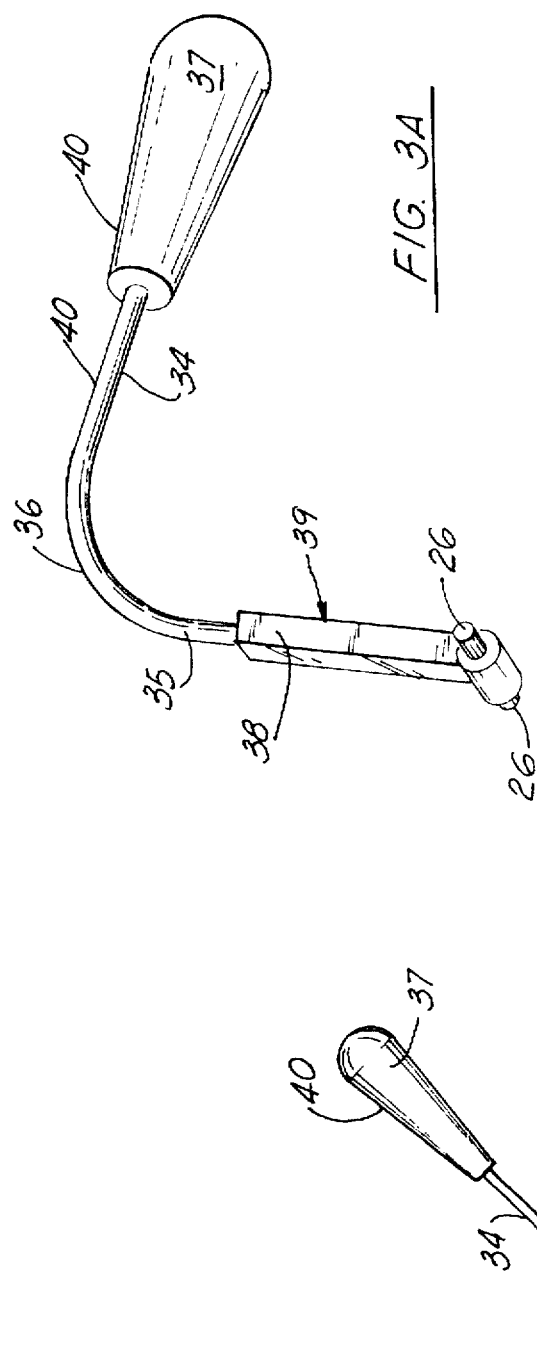
FIG. 3A is a perspective fragmentary view of the preferred embodiment of the apparatus of the present invention illustrating the actuator lever.
Figure 3:
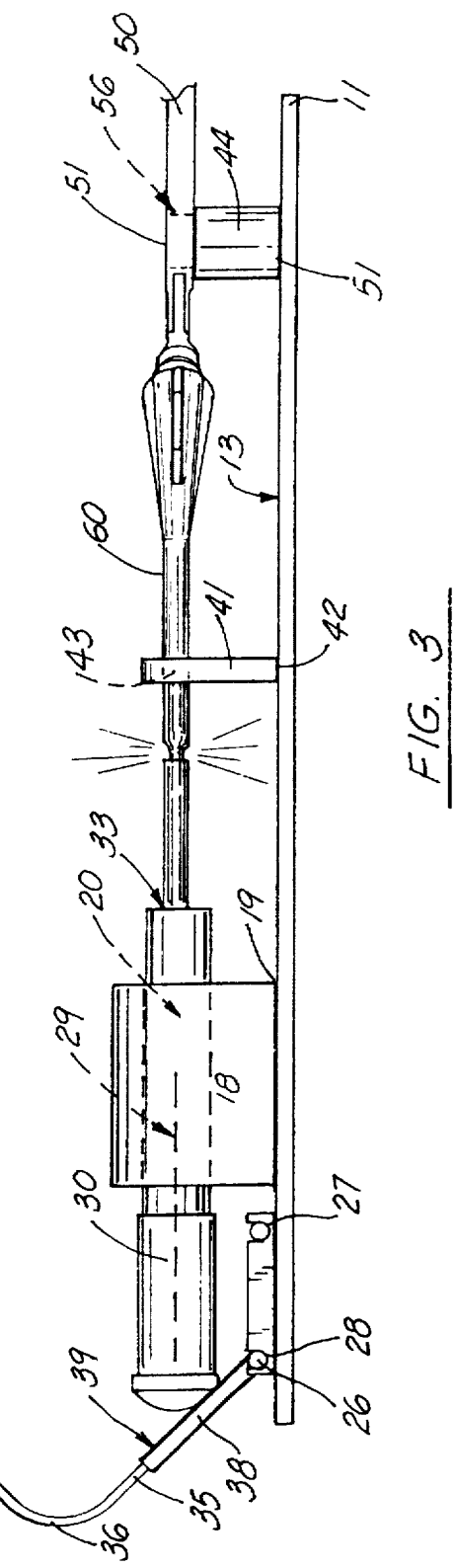
FIG. 3 is an elevational view of the preferred embodiment of the apparatus of the present invention showing the impacting of a distal extension member to a stem.

The base member 11 upper surface 13 supports a number of components that extend away from upper surface 13 as shown in FIGS. 1-3. These components include a first support 18 that is affixed by bolting or riveting for example at attachment 19 to base member 11. Support 18 provides a longitudinal bore 20 with a central longitudinal axis 29. During use, an impact driver tool 30 can be placed within bore 20 as shown in FIG. 3. It should be understood that the impact driver tool 30 is commercially available, sold by Smith & Nephew Richards of Memphis, Tenn.

Another component that extends away from upper surface 13 of base 11 is cleat 21. Cleat 21 is fastened to upper surface 13 of base 11 using a bolted connection, rivets, welding or the like. Cleat 21 can be generally rectangular in shape as shown and includes a number of attachment positions for affixing lever arm 40 (FIG. 3A) thereto. In FIGS. 1 and 3, two attachment positions 27, 28 are illustrated. Each attachment position 27, 28 is defined by a pair of spaced apart slots that are generally U-shaped. The attachment position 27 includes a pair of slots 22, 23. The attachment position 28 includes a pair of slots 24, 25. The lever arm 40 provides a lower transverse pin 26 that registers in the pair of slots 22,23 when attaching to the first attachment position 27. This first attachment position places the lever arm 40 transverse pin 26 closer to the support component 18.

In FIG. 3, the lever 40 has been attached to the second attachment position 28, a position that is farther away from the support component 18. These different attachment positions 27, 28 allow the lever arm 40 to be used to activate the impact driver tool 30 from different positions depending upon the overall length of a modular prosthesis to be assembled.

The impact driver tool 31 includes an upper end portion 31 and a lower end portion 32. The lower end 32 can provide a concave surface 33 for receiving one end portion of the handle 50 to be assembled.

Lever arm 40 can be L-shaped as shown in FIGS. 3 and 3A, providing straight sections 34, 35 and bent section 36. The upper most end portion of lever arm 40 provides a handle 37 to be gripped by the surgeon during use. The lower end of lever arm 40 provides a thickened portion 38 having a flat surface 39 for engaging the upper end 31 of impact driver tool 30 as shown in FIG. 3.

A support 41 defines a center support having an attachment 42 such as riveted or bolted to base 11. This support 41 provides a cylindrically shaped opening 43 for example that can be used to support the mid-portion of a handle 50 to be assembled as shown in FIG. 3.

A third support 44 is in the form of an end support. The support 44 can be sized and shaped to receive a handle member 50 that is used to manipulate certain prosthesis parts before and after assembly. The support 44 has an attachment 45 to base 11 using a bolted, riveted, or welded connection for example. Support 44 as shown in FIG. 4 includes a cube shaped portion 46 having an upper surface 47. A projection 48 extends above surface 47. The projection 48 includes a flat upper surface 49, a pair of flat side surfaces 51, 52, a curved side surface 53, and a pair of side flat surfaces 54, 55 that are on opposite sides of the curved side surface 53. The projection 49 registers in a corresponding shaped recess 56 of handle 50 as shown in FIGS. 1, 3 and 7-10.

In FIG. 7-10, the handle 50 has a sliding trigger 57 that can be operated by the surgeon. The trigger 57 has an end portion 58 that can be extended or retracted with respect to post 59. A cylindrically shaped opening through the post 59 and a portion of the handle 50 accommodates the elongated cylindrically shaped end portion 58 as shown in FIG. 7.

In order to form a connection between the handle 50 and a prosthesis part 60 such as for example a shoulder prosthesis part 60, the surgeon pulls the trigger 57 in the direction of arrows in FIG. 10 to retract end portion 58 of trigger 57. This allows post 58 to be placed within socket 62 of frustroconical connector 61. A hemispherical recess 63 within socket 62 receives the end portion 58 after the post 59 has registered in the socket 62. The user accomplishes registration of end portion 58 into hemispherical recess 63 by releasing the trigger 57, allowing a return spring (not shown) to move the trigger into the extended position shown in FIG. 7.

Once the user so assembles handle 50 and prosthesis part 60, the part 60 and handle 50 can be placed in the position as shown in FIGS. 1 and 3. In this position, the prosthesis part 60 extends through opening 43 of support 41. The handle 50 attaches to support 44 at recess 48 at handle 50 as shown in FIGS. 7 and 8.

The surgeon can then select a desired modular extension part 71 for assembly to the stem 68 of prosthesis part 60. The prosthesis parts 60 and 71 are joined at a taper lock connection 69. This is accomplished by providing each of the prosthesis parts 60 and 71 with tapered annular portions such as tapered annular male connector portion 70 and tapered annular female connection portion 72. Such a "taper lock" connection can be seen for example in the DeMane U.S. Pat. Nos. 4,995,883 and 5,108,452 incorporated herein by reference.

After the selected stem or extension member prosthesis part 71 is attached to the prosthesis part 60, the surgeon then places impact driver tool 30 within the bore 20 of support 18 as shown in FIG. 3. The entire assembly of handle 50, prothesis part 60, extension prosthesis part 71, and impact driver 30 are supported upon the plurality of supports 44, 41 and 18. The surgeon then places the lever 40 in a desired position depending upon the overall length of the assembly of prosthesis parts 60, 71 and impact driver 30. The lever 40 is positioned by placing the transverse pin 26 in a desired attachment position 27, 28 of cleat 21. The surgeon then rotates the lever arm 40 toward the center support 41, engaging the upper end 31 of impact driver 30 with the thickened portion 38 of lever arm 40. The flat surface 39 of lever arm 40 engages the upper end 31 of impact driver 30. This action compresses and shortens the impact driver 30 which triggers the impact load. During this transmission of the impact load to the prosthesis parts 60, 71 the entire axial load is carried by the base 11 and two components structurally attached thereto, namely the component 44 that supports and holds the handle 50 and the component lever arm 40 that is anchored to the cleat 21.

In FIGS. 2 and 5–6, there is shown an assembly of a prosthesis head 86 to shoulder prosthesis part 60. The shoulder prosthesis part 60 has a fin 64 with openings 66 as shown in FIGS. 6 and 7. In FIGS. 2 and 5–6, a pin 82 extends through auxiliary support 73 and through one of the openings 66 of fin 64 for supporting the prosthesis part 60 in the position shown in FIG. 6. The auxiliary support 73 can be fastened to the base member 11 or simply braced against support 41 as shown in FIGS. 2 and 6.

The auxiliary support 73 has a lower surface 74, upper surface 75, diagonal surface 76, rear surface 77 and side surfaces 78. A longitudinally extending slot 79 extends along the diagonal surface 76, approximately mid way between the side surfaces 78. The slot 79 receives the fin 64 of prosthesis part 60 as shown in FIG. 6. A pair of transverse aligned openings 80, 81 extend through the auxiliary support 73, communicating with the slot 79 as shown in FIG. 5. The openings 80,81 receive pin 82 that can be manipulated using handle 84. The end 83 of the pin 82 is first routed through the cylindrically shaped opening 80, then through an opening 66 through fin 64, and then through the cylindrically shaped opening 81.

After the prosthesis part 60 is secured as shown in FIG. 6, the head 86 can be assembled thereto. The frustroconical socket 87 of head 86 registers with and fits a similar corresponding frustroconical portion 61 of prothesis 60. The corresponding frustroconical portions 61, 87 form a taper lock connection once loaded. The surgeon first loosely fits the head 86 to the prosthesis parts 60 by forming a loose connection between the socket 87 and frustroconical portion 61.

In FIG. 2, the lower end 32 of impact driver 30 is placed against head 86 as shown. The surgeon then rotates the lever arm 40 as shown by the arrow 88 in FIG. 2 firing impact driver 30 and forcing the lower end 32 against the head 86 with the impact force to assemble the components 86, 60 together. In FIG. 2, arrow 89 illustrates the direction of axial load that is transmitted from the impact driver 30 to the head 86, forming a taper lock connection between the head 86 and prosthesis part 60. This assembly of the parts 86, 60 is with a predictable axial load because the load is transmitted to the base member 11 via the support 41 and the lever arm 40 attached to cleat 21.

Within the teaching of the present invention, other auxiliary support 73 could be provided for forming an attachment to a desired prosthesis part for holding that prosthesis part in alignment with another prosthesis part during impact loading using the apparatus of the present invention.

The following table lists the parts numbers and parts descriptions as used herein and in the drawings attached hereto.

PARTS LIST

| Part Number | Description |
| --- | --- |
| 10 | prosthesis impactor apparatus |
| 11 | base member |
| 12 | periphery |
| 13 | upper surface |
| 14 | end |
| 15 | end |
| 16 | side |
| 17 | side |
| 18 | end support |
| 19 | attachment |
| 20 | longitudinal bore |
| 21 | cleat |
| 22 | slot |
| 23 | slot |
| 24 | slot |
| 25 | slot |
| 26 | transverse pin |
| 27 | attachment position |
| 28 | attachment position |
| 29 | axis |
| 30 | impact driver tool |
| 31 | upper end |
| 32 | lower end |
| 33 | concavity |
| 34 | straight section |
| 35 | straight section |
| 36 | bent section |
| 37 | handle |
| 38 | thickened portion |
| 39 | flat surface |
| 40 | lever |
| 41 | center support |
| 42 | attachment |
| 43 | opening |
| 44 | end support |
| 45 | attachment |
| 46 | cube |
| 47 | upper surface |
| 48 | projection |
| 49 | upper flat surface |
| 50 | handle |
| 51 | flat side |
| 52 | flat side |
| 53 | curved side |
| 54 | flat side |
| 55 | flat side |
| 56 | recess |
| 57 | sliding trigger |
| 58 | end portion |
| 59 | post |
| 60 | prosthesis part |
| 61 | frustroconical connector |
| 62 | socket |
| 63 | hemispherical recess |
| 64 | fin |
| 65 | fin |
| 66 | opening |
| 67 | opening |
| 68 | cylindrical stem |
| 69 | taper lock connection |
| 70 | male connector |
| 71 | extension part |
| 72 | female connector |
| 73 | auxiliary support |
| 74 | lower surface |
| 75 | upper surface |
| 76 | diagonal surface |
| 77 | rear surface |
| 78 | side surfaces |
| 79 | slot |
| 80 | transverse opening |
| 81 | transverse opening |
| 82 | pin |
| 83 | end |
| 84 | handle |
| 85 | arrows |
| 86 | head |
| 87 | frustroconical socket |
| 88 | arrow |
| 89 | arrow |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. Modular orthopedic prosthesis parts and an impactor apparatus for assembling modular orthopedic prosthesis parts comprising;
   a) a base member defining a plane and having a plurality of components extending away from said plane;
   b) said components including a pair of spaced apart supports;
   c) an impactor driver tool removably supported upon said supports in a fixed position relative to the base member;
   d) said components including an impactor driver tool actuator that pivotally attaches to the base member;
   e) the modular prosthesis parts being connectable at a taper lock connection defined by respective tapered annular portions of the prosthesis parts;
   f) means for holding the prosthesis parts adjacent the base in axial alignment with the impact driver, in between the pair of supports; and
   g) said actuator defining means for activating the impact driver tool to transmit a load to the prosthesis parts for driving said parts together at the taper lock connection;
   h) wherein the spaced apart supports hold opposite end portions of the assembly of prosthesis parts and impact driver;
   i) wherein the base member and its components carry axial load transmitted from the impact driver to the prosthesis so that the axial load is reproducible and accurate notwithstanding the rigidity of any underlying surface adjacent the base member.

2. The apparatus of claim 1 wherein said impactor tool is an elongated tool body having a trigger at one end portion thereof.

3. The apparatus of claim 1 wherein the components include a pivot on the base and a lever that rotates about the pivot, said lever being positioned to engage one end portion of the impactor when the impactor is held by the components and one of the components axially opposes force applied to the impactor using the lever.

4. The apparatus of claim 1 wherein one of the components is a support with an opening therethrough.

5. The apparatus of claim 1 wherein there are a plurality of pivots and the actuator is a lever that can be selectively attached to one of the pivots.

6. The apparatus of claim 1 wherein the base is a metal plate member and the supports are of a plastic material.

7. The apparatus of claim 1 wherein the prosthetic parts include a humeral prosthesis member with a stem, an extension sleeve with a bore that fits over the stem, and a head that connects to the stem generally opposite the extension sleeve.

8. The apparatus of claim 1 wherein the prosthesis is adapted for placement in the intramedullary canal of a patient.

9. The apparatus of claim 1 wherein the prosthesis includes a stem and an extension sleeve, each having cooperating frustroconical portions that connect to define a taper lock connection.

10. A method of joining a pair of prosthesis parts that are connectable at a taper lock connection defined by respective tapered annular portions of the prosthesis parts comprising the steps of:
   a) aligning the respective tapered annular portions of the prosthesis parts;
   b) fitting the respective annular tapered portions together;
   c) holding the respective tapered annular portions together with spaced apart components anchored to a base member;
   d) supporting an impact driver in a position that aligns the central axis of the impact driver with the respective annular portions;
   e) using one of the components to hold one end of the assembly of prosthesis parts opposite the impact driver;
   f) using a second of the components to hold a second end of the assembly of prosthesis parts and the impact driver;
   g) compressing the prosthesis parts together with the impact driver;
   h) wherein in step "g", one of the components is movably mounted to the base member in relation to the other component for activating the impact driver, so that when the impact driver is activated, an impact load is transmitted to the respective annular portions.

* * * * *